(12) United States Patent
Nun (10) Patent No.: US 7,976,520 B2
(45) Date of Patent: Jul. 12, 2011

(54) EYE WALL ANCHORED FIXTURES

(75) Inventor: Joshua Ben Nun, Kfar Vitkin (IL)

(73) Assignee: Nulens Ltd., Herzliya Pituah (IL)

(*) Notice: Subject to any disclaimer, the term of this patent is extended or adjusted under 35 U.S.C. 154(b) by 1210 days.

(21) Appl. No.: 11/483,532

(22) Filed: Jul. 11, 2006

(65) Prior Publication Data

US 2006/0253151 A1 Nov. 9, 2006

Related U.S. Application Data

(63) Continuation-in-part of application No. PCT/IL2005/00003, filed on Jan. 3, 2005.

(60) Provisional application No. 60/759,060, filed on Jan. 17, 2006.

(30) Foreign Application Priority Data

Jan. 12, 2004 (IL) .................................. 159818

(51) Int. Cl.
*A61M 35/00* (2006.01)
*A61M 31/00* (2006.01)
*A61K 9/22* (2006.01)
*A61F 2/14* (2006.01)
*A61F 2/00* (2006.01)

(52) U.S. Cl. ............ 604/294; 604/300; 604/891.1; 604/521; 623/4.1; 424/427

(58) Field of Classification Search .......... 604/9, 521, 604/300, 294, 891.1; 600/475; 606/185, 606/219; 424/427, 473
See application file for complete search history.

(56) References Cited

U.S. PATENT DOCUMENTS

| 3,845,770 A | 11/1974 | Theeuwes et al. |
| 3,962,414 A | 6/1976 | Michaels |
| 5,098,443 A | 3/1992 | Parel et al. |
| 5,466,233 A | 11/1995 | Weiner et al. |
| 5,830,173 A * | 11/1998 | Avery et al. ............. 604/9 |
| 5,980,548 A | 11/1999 | Evans |
| 6,203,556 B1 * | 3/2001 | Evans et al. ............ 606/185 |

(Continued)

FOREIGN PATENT DOCUMENTS

DE 10005957 8/2001

(Continued)

OTHER PUBLICATIONS

Japanese Office Action, Apr. 1, 2011.

*Primary Examiner* — Kevin C Sirmons
*Assistant Examiner* — Bradley G Thomas, Jr.
(74) *Attorney, Agent, or Firm* — Morgan Lewis & Bockius LLP (57) ABSTRACT

Eye wall anchored fixtures each including at least one elongated anchor member for driven lengthwise insertion into an eye's eye wall in a transverse direction to its thickness for supporting an intraocular device in the eye's vitreous cavity. Fixtures are preferably anchored in circumferential incisions in a human adult eye's pars plana preferably 3.5 mm posterior to its corneal limbus, and perpendicular to a circumferential incision. The fixtures are either generally L-shaped with a single elongated anchor member designed for withdrawal from an eye wall or self-anchoring thereinto, or generally T-shaped with a pair of oppositely directed self-anchoring elongated anchor members for sealing a throughgoing incision. Intraocular devices can be designed for intraocular drug delivery, for acquiring intraocular physiological measurements, and the like.

16 Claims, 6 Drawing Sheets

U.S. PATENT DOCUMENTS

| | | |
|---|---|---|
| 6,241,747 B1 | 6/2001 | Ruff |
| 6,299,895 B1 * | 10/2001 | Hammang et al. ............ 424/427 |
| 6,331,313 B1 | 12/2001 | Wong et al. |
| 6,713,081 B2 | 3/2004 | Robinson et al. |
| 6,719,750 B2 | 4/2004 | Varner et al. |
| 6,756,049 B2 | 6/2004 | Brubaker et al. |
| 7,033,605 B2 | 4/2006 | Wong |
| 7,181,287 B2 | 2/2007 | Greenberg et al. |
| 2001/0008969 A1 | 7/2001 | Evans et al. |
| 2002/0110591 A1 | 8/2002 | Brubaker et al. |
| 2003/0014036 A1 | 1/2003 | Varner et al. |
| 2003/0175324 A1 | 9/2003 | Robinson et al. |
| 2005/0031669 A1 | 2/2005 | Shafiee et al. |
| 2005/0055014 A1 | 3/2005 | Coppeta et al. |
| 2005/0137538 A1 | 6/2005 | Kunzler et al. |
| 2005/0244461 A1 | 11/2005 | Nivaggioli et al. |
| 2005/0244465 A1 | 11/2005 | Nivaggioli et al. |
| 2006/0013835 A1 | 1/2006 | Anderson et al. |
| 2006/0067979 A1 | 3/2006 | Kunzler et al. |
| 2006/0110429 A1 | 5/2006 | Reiff et al. |
| 2006/0167435 A1 | 7/2006 | Adamis et al. |
| 2006/0229585 A1 | 10/2006 | Peyman |
| 2006/0257450 A1 | 11/2006 | Mudumba et al. |
| 2007/0016074 A1 * | 1/2007 | Abreu ..................... 600/475 |

FOREIGN PATENT DOCUMENTS

| | | |
|---|---|---|
| EP | 0251680 | 1/1988 |
| SU | 980711 | 12/1982 |
| WO | WO-9405257 | 3/1994 |
| WO | WO 01/68016 | 9/2001 |
| WO | WO 02/100318 | 12/2002 |
| WO | WO02100318 | 12/2002 |
| WO | WO03092564 | 11/2003 |
| WO | WO-2005065600 | 7/2005 |

* cited by examiner

EYE WALL ANCHORED FIXTURES

CROSS-REFERENCE TO RELATED APPLICATIONS

This application is a United States Continuation-In-Part (CIP) application of PCT International Application PCT/IL2005/000003 having an international filing date of 3 Jan. 2005 and designating the United States, the contents of which are hereby incorporated by reference in their entirety.

This application also claims the benefit of prior U.S. provisional patent application No. 60/759,060 filed 17 Jan. 2006, the contents of which are hereby incorporated by reference in their entirety.

FIELD OF THE INVENTION

The invention pertains to eye wall anchored fixtures.

BACKGROUND OF THE INVENTION

Certain eye conditions including inter alia Age related Macular Degeneration (AMD), diabetic macular edema, uveitis, and the like, require specific drug quantities at regular intervals for undetermined periods of time. Shots of specific drug quantities are administered at the present time by intraocular injection notwithstanding that they are traumatic and can lead to eye infections, and other undesirable complications.

Conventional intraocular drug dispensers include a drug reservoir from which a drug is released by diffusion or osmosis through a membrane for continuously administering drugs into an eye's vitreous cavity over relatively prolonged periods of time. However, the operation of such intraocular drug dispensers are often impeded by natural fibrous tissue growing thereon resulting in their actual drug delivery rate being lower than their intended drug delivery rate or even completely blocked to the detriment of an intended treatment.

U.S. Pat. No. 5,098,443 to Parel et al. illustrates and describes intraocular and intraorbital implantable devices for the controlled release of pharmacological agents. U.S. Pat. No. 5,466,233 to Weiner et al. illustrates and describes an intraocular drug delivery tack for transversing an eye's pars plana for administering a drug to the eye's vitreous cavity. U.S. Pat. No. 5,830,173 to Avery et al illustrates and describes an intravitreal medicine delivery system device for administering a drug to an eye's vitreous cavity. US Patent Application Publication No. US 2002/0110591 to Brubaker et al. illustrates and describes a sustained release drug delivery device for suturing to an eye wall.

SUMMARY OF THE INVENTION

The present invention is for eye wall anchored fixtures having at least one elongated anchor member for driven lengthwise insertion into an eye wall for supporting an intraocular device in the eye's vitreous cavity. Fixtures are intended for implantation in a circumferential segment of an eye wall devoid of retinal tissue and blood vessels called the pars plana The width of an average human adult eye's pars plana increases from a minimum width $W_N$ of about 1 mm towards his nose to a maximum width $W_T$ of about 2 mm towards his temporal region. Fixtures are preferably anchored in circumferential incisions in a human adult eye's pars plana preferably 3.5 mm posterior to its corneal limbus, perpendicular to a circumferential incision, and in a transverse direction to the eye wall's thickness. Fixtures are preferably anchored temporally since an eye's pars plana is not only wider but also more accessible.

Fixtures can be designed for withdrawal, or as a self-anchoring implant, or as a sealing self-anchoring implant for sealing a throughgoing incision by drawing two opposing side walls of an incision together. Fixtures can be integrally formed with intraocular devices designed for intraocular drug administration, for acquiring intraocular physiological measurements for monitoring and/or diagnostic purposes, for example, a pressure sensor for monitoring glaucoma, and the like. Alternatively, fixtures can be formed with attachment devices whereby three or more fixtures deployed peripherally around an eye's pars plana are capable of supporting a relatively massive intraocular device in an eye's vitreous cavity.

Intraocular drug dispensers preferably include an elongated support member having a multitude of discrete drug containing capsules therealong which are intended to individually release their contents into an eye's vitreous cavity, and sealing self-anchoring T-shaped fixtures at the opposite ends of their elongated support members. The drug containing capsules can be formed from self degradable biocompatible material enabling drug release after a predetermined time depending on material thickness and rate of material degradation. Alternatively, the drug containing capsules can be formed from non degradable biocompatible material intended for rupturing by external means, for example, laser radiation, ultrasonic waves, and the like.

BRIEF DESCRIPTION OF THE DRAWINGS

In order to understand the invention and to see how it can be carried out in practice, preferred embodiments will now be described, by way of non-limiting examples only, with reference to the accompanying drawings in which similar parts are likewise numbered, and in which.

DETAILED DESCRIPTION OF PREFERRED EMBODIMENTS OF THE PRESENT INVENTION

Figures 1, 2:
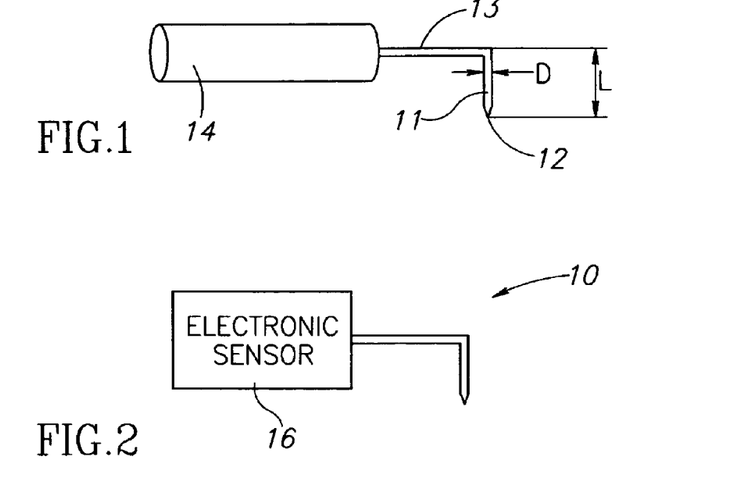
FIG. 1 is a pictorial view showing an eye wall anchored L-shaped fixture with a drug release capsule for intraocular drug administration.
FIG. 2 is a pictorial view showing an eye wall anchored L-shaped fixture with an electronic sensor for acquiring intraocular physiological measurements.
Figure 3:
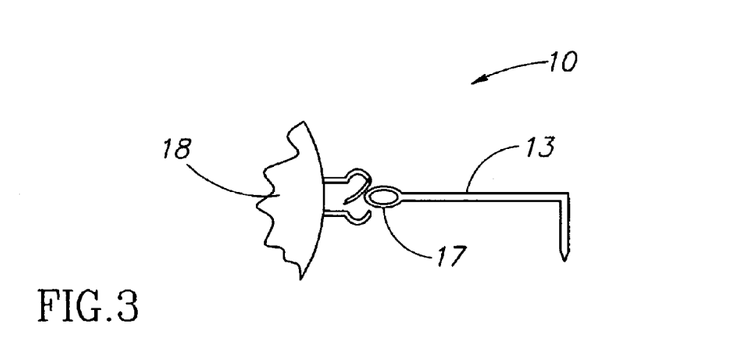
FIG. 3 is a pictorial view showing an eye wall anchored L-shaped fixture with an attachment device for supporting a discrete intraocular device in an eye's vitreous cavity.

FIGS. 1-3 show eye wall anchored L-shaped fixtures 10 having a generally L-shaped structure including an elongated anchor member 11 with a pointed leading end 12, and a support member 13. The anchor members 11 have a length L in the range of about 1 mm to about 3 mm, and preferably 2 mm±0.5 mm, and a diameter D in the range of about 100 μm to about 200 μm, and preferably 150 μm±10 μm. The fixtures 10 are made from a biocompatible material suitable for implantation in an eye wall, and preferably stainless steel so as to be enable slight resilient deformation from their preferred right angle configuration for facilitating some flexibility to deploy an intraocular device in a preferred location in an eye's vitreous cavity. The support member 13 can be provided with a drug release capsule 14 for intraocular drug administration (see FIG. 1), an electronic sensor 16 for acquiring intraocular measurements for monitoring and/or diagnostic purposes (see FIG. 2), and the like. Alternatively, a support member 13 can terminate in an attachment device 17 for supporting a discrete intraocular device 18 (see FIG. 3). The attachment devices 17 can be implemented by loops, hooks, clips, and the like.

Figure 4:
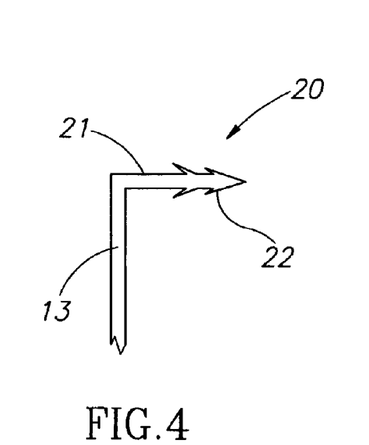
FIG. 4 is a pictorial view showing a self-anchoring member of a self-anchoring L-shaped fixture.

FIG. 4 shows an eye wall anchored L-shaped fixture 20 having a similar construction as a fixture 10 but with a self-anchoring anchor member 21 having a self-anchoring leading end 22 for anchoring the fixture 20 in an eye's pars plana on its driven lengthwise insertion there into. The leading end 22 can be barbed, hook shaped, and the like.

Figure 5:
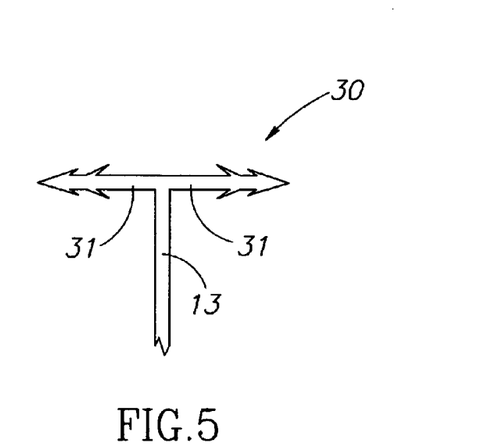
FIG. 5 is a pictorial view showing oppositely directed self-anchoring members of a sealing self-anchoring T-shaped fixture.

FIG. 5 shows an eye wall anchored T-shaped fixture 30 having a similar construction as a fixture 10 but with a pair of oppositely directed self-anchoring elongated anchor members 31. The fixture 30 can be employed for sealing a throughgoing incision through which it is implanted in an eye by virtue of the anchor members 31 being inserted into opposite side walls of the throughgoing incision so as to draw them together.

Figure 6:
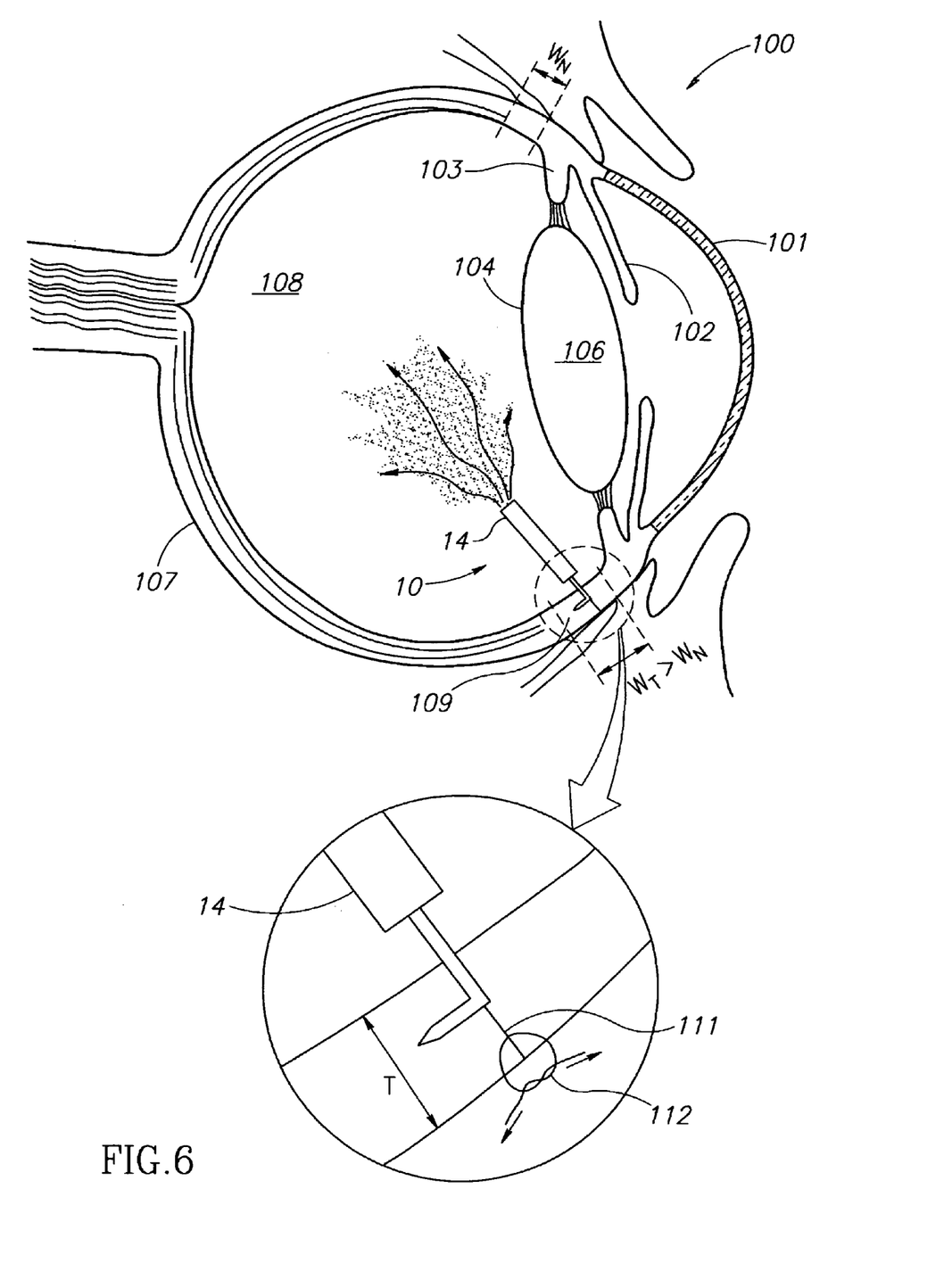
FIG. 6 is a horizontal cross section of a human eye showing FIG. 1's fixture anchored in the eye's pars plana together with a close-up of the anchoring site.

FIG. 6 shows an eye 100 having a cornea 101, an iris 102, a ciliary body 103 supporting a capsular bag 104 with a natural lens 106, an eye wall 107, and a vitreous cavity 108. The eye wall 107 includes a circumferential pars plana 109 whose width increases from a minimum width $W_N$ of about 1 mm to a maximum width $W_T$ of about 2 mm, and which has a largely uniform thickness T of about 1 mm. A circumferential incision 111 is made in the pars plana 109 about 3.5 mm posterior to its corneal limbus and the fixture 10 is implanted in the eye 100 with its anchor member 11 driven lengthwise thereinto perpendicular to the incision 111 for supporting the drug release capsule 14 in the eye's vitreous cavity 108. The incision 111 is closed with a suture 112.

Figure 7:
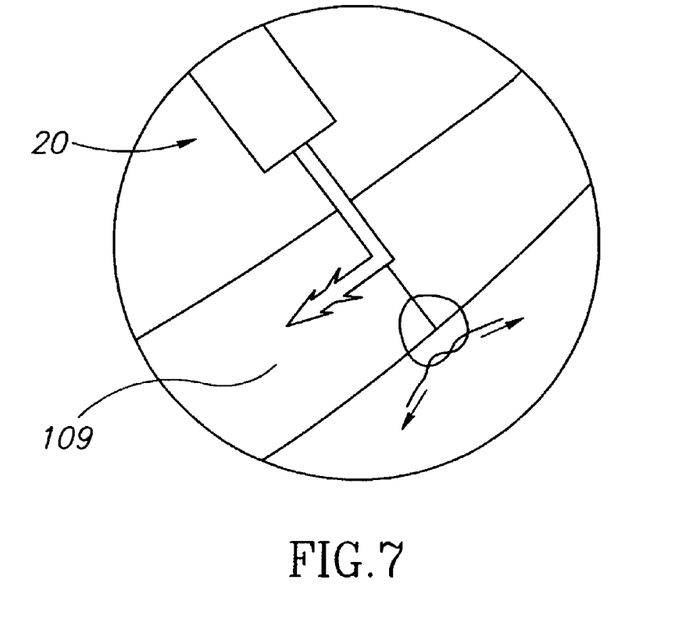
FIG. 7 is a pictorial close-up showing the anchoring of a FIG. 4 type fixture in a sutured circumferential incision formed in an eye's pars plana.
Figure 8:
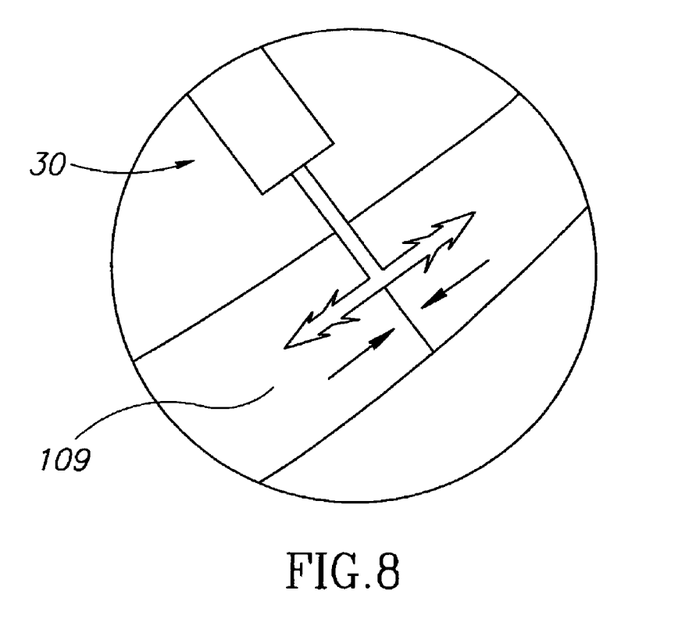
FIG. 8 is a pictorial close-up showing the anchoring of a FIG. 5 type fixture in an eye's pars plana for sealing a circumferential incision.
Figure 9:
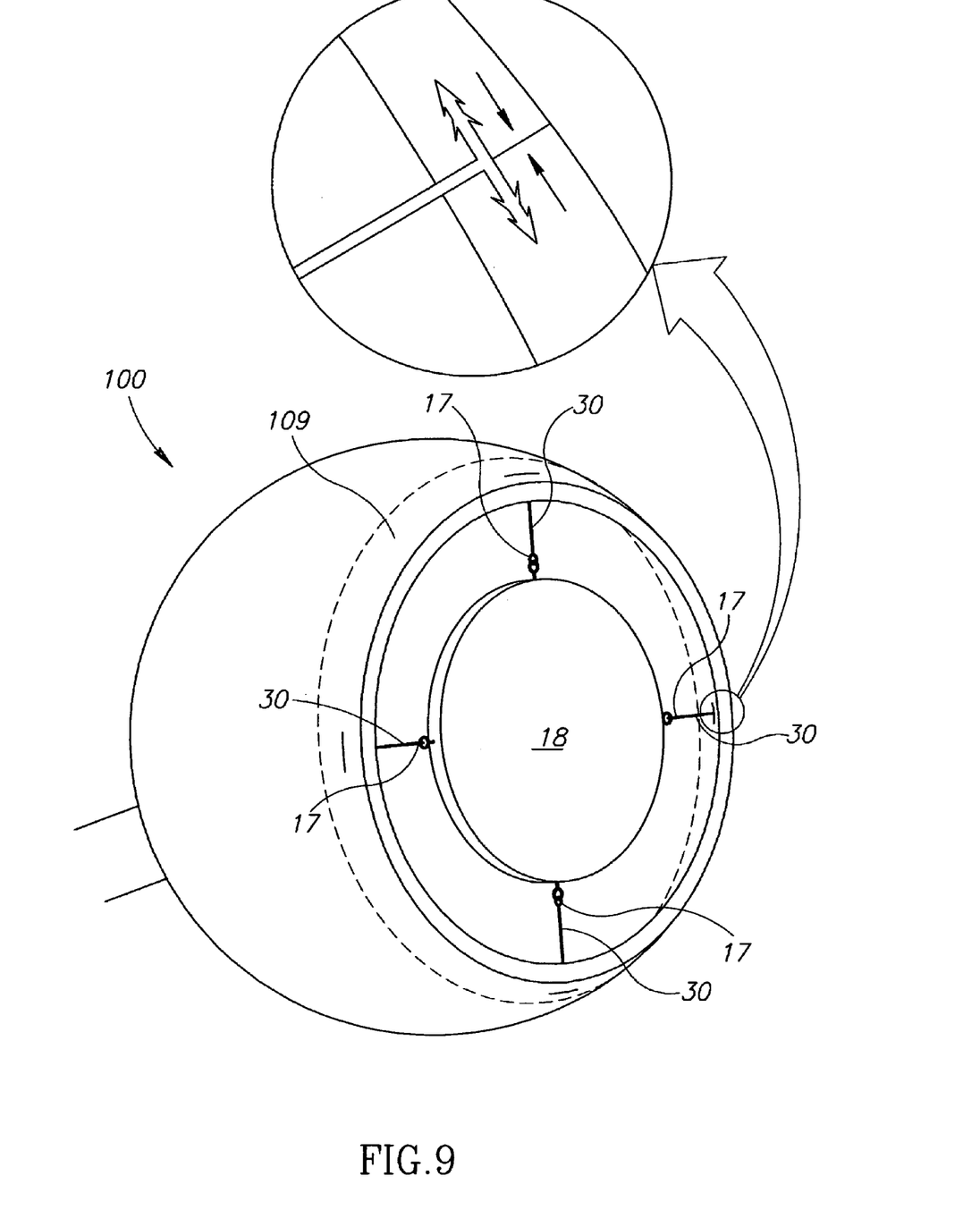
FIG. 9 is a pictorial representation of a human eye showing four FIG. 5 type fixtures implanted in the eye's pars plana for supporting an intraocular device in the eye's vitreous cavity, and a close-up of one of the fixtures sealing a circumferential incision.

FIG. 7 shows a fixture 20 anchored in an eye's pars plana 109 also with a suture for closing the circumferential incision through which it is implanted. FIG. 8 shows a fixture 30 anchored in an eye's pars plana 109 for drawing the side walls on either side of a circumferential; incision towards one another for enabling an eye to seal itself without the need for a suture. FIG. 9 shows four fixtures 30 with attachment devices 17 deployed at 0°, 90°, 180°, and 270° deployed peripherally around an eye's pars plana 109 for supporting an intraocular device 18 in an eye's vitreous cavity.

Figure 10:
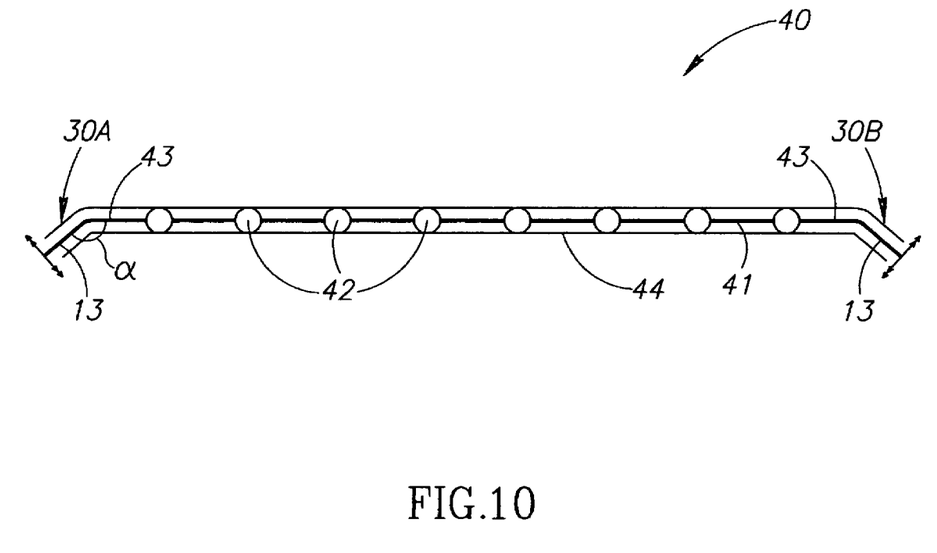
FIG. 10 is a pictorial view of an intraocular drug dispenser with a multitude of discrete drug containing capsules for individually releasing their contents.

FIG. 10 shows an intraocular drug dispenser 40 including an elongated support member 41 with a multitude of discrete drug containing capsules 42, and a pair of opposite ends 43 with fixtures 30A and 30B for securely mounting the intraocular drug dispenser 40. The support member 41 and the fixtures 30A and 30B are made from a suitable biocompatible material for implantation in an eye wall, and preferably stainless steel for enabling slight resilient deformation for facilitating deploying an intraocular drug dispenser 40 in a preferred location in an eye's vitreous cavity. The support member 41 has a total length in the region of 30 mm such that it can be bowed into a horse shoe shape in situ to minimize visual disruption on implantation in an eye. The fixtures 30A and 30B each have a support member 13 subtending an obtuse angle α≈170° with respect to the support member 41 for assisting in implanting the intraocular drug dispenser 40 in an eye. The drug containing capsules 42 can be enclosed by a soft silicone sheath 44 for protecting an eye's delicate internal structures on pulling the support member 41 through an eye from one scleral incision to an opposite scleral incision.

The drug containing capsules 42 have exterior shells made from suitable biocompatible material. Such shells can be formed from self degradable biocompatible material of different material thickness and/or rate of material degradation for controlling the release of their contents at predetermined times. Alternatively, such shells can be formed from non degradable biocompatible material intended for individual rupturing effected by local heating, local shock waves, and the like. In the latter case, a physician can employ any standard contact lens for peripheral retina inspection for assisting him in directing a laser beam towards a drug containing capsule for rupturing same. A physician may rupture two drug containing capsules 42 simultaneously to double the drug dosage to a particular patient depending on his clinical condition.

Figure 11:
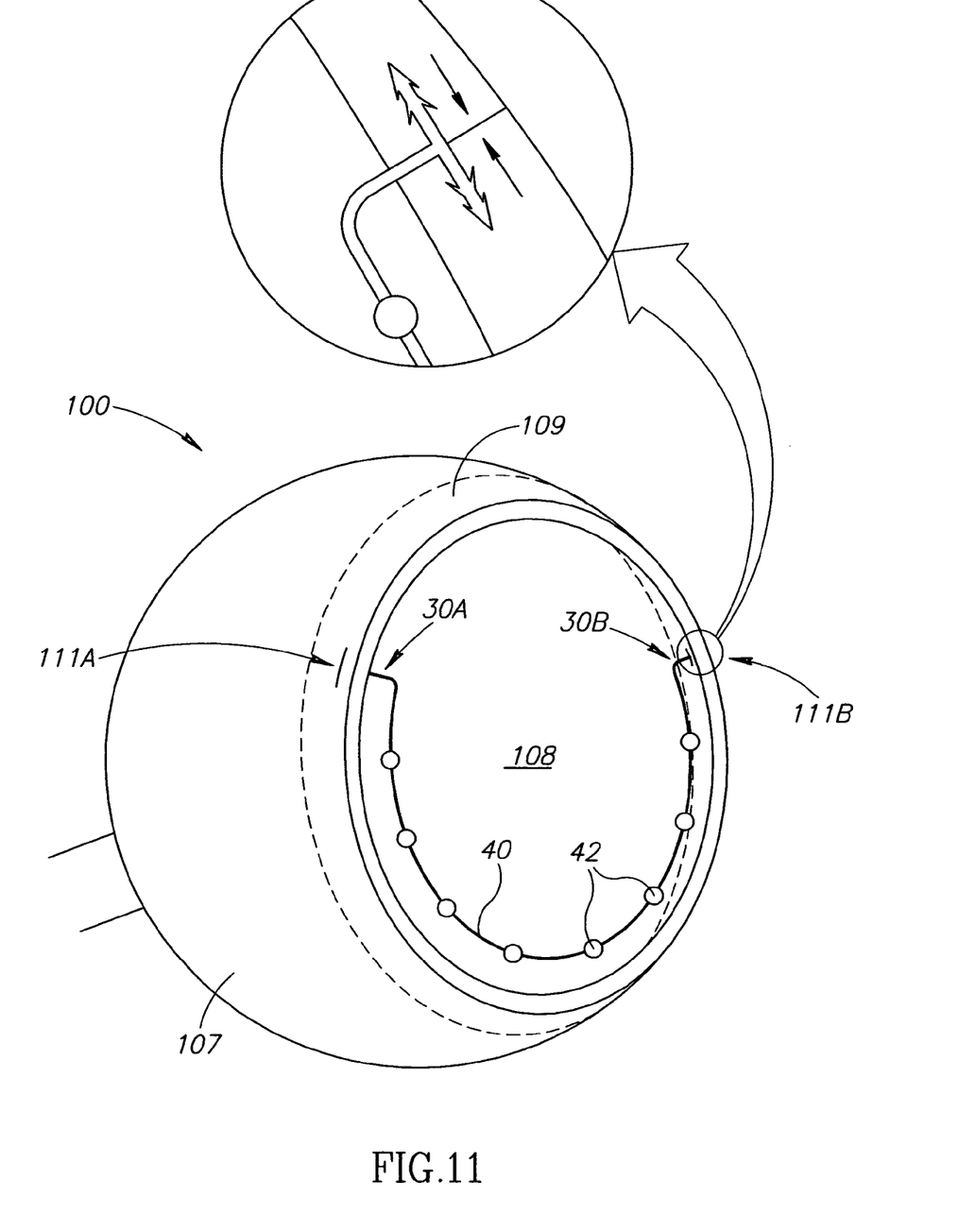
FIG. 11 is a pictorial representation of a human eye with FIG. 10's intraocular drug dispenser implanted in the eye's pars plana for releasing medication into the eye's vitreous cavity, and a close-up of one of the intraocular drug dispenser's fixtures sealing a circumferential incision.

Implantation of the intraocular drug dispenser 40 in a suitably prepared eye 100 is as follows: An eye surgeon threads the intraocular drug dispenser 40 with its soft silicone sheath 44 intact from a throughgoing circumferential incision 111A made in the pars plana 109 to an opposite throughgoing circumferential incision 111B. The eye surgeon removes the soft silicone sheath 44. The eye surgeon inserts the fixture 30A into opposite side walls of the incision 111A so as to draw them together. The eye surgeon bends the support member 41 downwards from fixture 30A and inserts the fixture 30B into the opposite side walls of the incision 111B so as to draw them together. The support member 41 only marginally disrupts vision, if at all.

While the invention has been described with respect to a limited number of embodiments, it will be appreciated that many variations, modifications and other applications of the invention can be made within the scope of appended claims.

The invention claimed is:

1. An eye wall anchored fixture for implantation in an eye having an eye wall with inner and outer surfaces and a vitreous cavity, the fixture comprising an L-shaped element including at least one elongated anchor member for driven lengthwise insertion of said one anchor member into the eye wall so that said one anchor member extends and is completely embedded lengthwise in the eye wall tissue, in a direction substantially transverse to the dimension between the inner and outer surfaces of the eye wall, each said at least one elongated anchor member having a length in the range of about 1 mm to about 3 mm, and a diameter in the range of about 100 μm to about 200 μm, and a support member mounted on said at least one elongated anchor member for supporting an intraocular device in the eye's vitreous cavity.

2. The fixture according to claim 1 wherein said length is in the range of 2 mm±0.50 mm.

3. The fixture according to claim 1 wherein said diameter is in the range of 150 μm±10 μm.

4. The fixture according to claim 1 wherein said at least one elongated anchor member includes a single elongated anchor member with a self-anchoring leading end for anchoring the fixture in an eye wall on its driven lengthwise insertion there into.

5. The fixture according to claim 1 wherein said L-shaped anchor member comprises a second anchor portion to form a T-shaped anchor member that includes a pair of oppositely directed elongated anchor portions, each with a self-anchoring leading end whereby the fixture is capable of sealing a throughgoing incision in an eye wall via which it is implanted therein.

6. The fixture according to claim 1 wherein said support member is integrally formed with said intraocular device.

7. The fixture according to claim 6 wherein said intraocular device administers an intraocular drug.

8. The fixture according to claim 6 wherein said intraocular device acquires intraocular physiological measurements.

9. The fixture according to claim 1 wherein said support member includes an attachment device for supporting a discrete intraocular device in an eye's vitreous cavity.

10. The fixture according to claim 1 wherein said support member includes a multitude of discrete drug containing capsules therealong for individually releasing their contents into an eye's vitreous cavity.

11. The fixture according to claim 10 wherein said support member includes sealing self-anchoring fixtures at its opposite ends.

12. The fixture according to claim 10 wherein said multitude of discrete drug containing capsules are enclosed by a soft silicone sheath.

13. The fixture according to claim 10 wherein said drug containing capsules have external shells formed from self degradable biocompatible material for controlled drug release.

14. The fixture according to claim 10 wherein said drug containing capsules have external shells formed from non degradable biocompatible material intended for selective rupturing by external means.

15. A method for anchoring a fixture for a implantation of an intraocular device in an eye having an eye wall with inner and outer surfaces and a vitreous cavity, comprising the steps of inserting an L-shaped element including at least one elongated anchor member by inserting said anchor member lengthwise into the eye wall so that said one anchor member extends and is completely embedded lengthwise in the eye wall tissue in a direction substantially transverse to the dimension between the inner and outer surfaces of the eye wall.

16. The method according to claim 15 wherein said L-shaped anchor member comprises a second anchor portion to form a T-shaped anchor member that includes a pair of oppositely directed elongated anchor portions, each with a self-anchoring leading end whereby the fixture is capable of sealing a throughgoing incision in an eye wall via which it is implanted therein.

* * * * *